US009822080B2

(12) United States Patent
Zák et al.

(10) Patent No.: US 9,822,080 B2
(45) Date of Patent: *Nov. 21, 2017

(54) $N^\alpha$, $N^\alpha$, $N^\alpha$-TRIALKYL HISTIDINE DERIVATIVES USEFUL FOR THE PREPARATION OF ERGOTHIONEINE COMPOUNDS

(71) Applicants: Mironova Innovations, LLC, Fairfield, NJ (US); Jan Trampota, Fairfield, NJ (US)

(72) Inventors: Bohumil Zák, Neratovice (CZ); Marie Záková, Neratovice (CZ); Jan Trampota, West Orange, NJ (US); John Olszewski, Tappan, NY (US); Theodore Gribb, III, Montclair, NJ (US)

(73) Assignees: MIRONOVA INNOVATIONS, LLC, Fairfield, NJ (US); Jan Trampota, Fairfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,293

(22) Filed: Jul. 26, 2016

(65) Prior Publication Data

US 2017/0050933 A1    Feb. 23, 2017

Related U.S. Application Data

(63) Continuation of application No. 15/068,687, filed on Mar. 11, 2016, now Pat. No. 9,428,463.

(60) Provisional application No. 62/173,895, filed on Jun. 10, 2015, provisional application No. 62/133,165, filed on Mar. 13, 2015.

(51) Int. Cl.
*C07D 233/84* (2006.01)
*C07C 269/00* (2006.01)
*C07C 221/00* (2006.01)
*C07C 225/06* (2006.01)
*C07C 271/12* (2006.01)

(52) U.S. Cl.
CPC .......... *C07D 233/84* (2013.01); *C07C 221/00* (2013.01); *C07C 225/06* (2013.01); *C07C 269/00* (2013.01)

(58) Field of Classification Search
CPC ... C07D 233/84; C07C 269/00; C07C 221/00; C07C 225/06; C07C 271/12
See application file for complete search history.

(56) References Cited

U.S. PATENT DOCUMENTS

| | | |
|---|---|---|
| 5,272,166 A | 12/1993 | Breslow et al. |
| 5,438,151 A | 8/1995 | Yadan et al. |
| 5,468,486 A | 11/1995 | Reddick et al. |
| 5,843,481 A | 12/1998 | Cruz |
| 5,871,779 A | 2/1999 | Cruz |
| 5,952,267 A | 9/1999 | Mottram |
| 5,972,840 A | 10/1999 | Mottram |
| 6,056,965 A | 5/2000 | Yadan et al. |
| 6,103,746 A | 8/2000 | Yarosh |
| 6,127,167 A | 10/2000 | Maruyama et al. |
| 6,183,769 B1 | 2/2001 | Campbell et al. |
| 6,261,606 B1 | 7/2001 | Mirksy et al. |
| 6,348,453 B1 | 2/2002 | Ben-Hur |
| 6,451,771 B1 | 9/2002 | Henderson et al. |
| 6,479,533 B1 | 11/2002 | Yarosh |
| 6,555,141 B1 | 4/2003 | Corson et al. |
| 6,863,906 B2 | 3/2005 | Henderson et al. |
| 7,297,500 B2 | 11/2007 | Hsieh et al. |
| 7,563,779 B2 | 7/2009 | Henderson et al. |
| 7,767,826 B2 | 8/2010 | Trampota |
| 8,140,156 B2 | 3/2012 | Zhang et al. |
| 8,399,500 B2 | 3/2013 | Erdelmeier |
| 8,410,156 B2 | 4/2013 | Yarosh |
| 8,933,245 B2 | 1/2015 | Yarosh |
| 2002/0042438 A1 | 4/2002 | Pelletier et al. |
| 2004/0047823 A1 | 3/2004 | Catroux et al. |
| 2011/0160268 A1 | 6/2011 | Repine |
| 2012/0128711 A1 | 5/2012 | Hausman et al. |
| 2012/0141611 A1 | 6/2012 | Landes et al. |
| 2012/0171156 A1 | 7/2012 | Basketter et al. |
| 2012/0282202 A1 | 11/2012 | Clapposen |
| 2013/0052315 A1 | 2/2013 | Tiwari et al. |
| 2014/0017182 A1 | 1/2014 | Trumbore et al. |
| 2014/0065132 A1 | 3/2014 | Hsiao et al. |
| 2014/0128615 A1 | 5/2014 | Yarosh |
| 2014/0158148 A1 | 6/2014 | Mette et al. |
| 2014/0363379 A1 | 12/2014 | Hausman |
| 2015/0073027 A1 | 3/2015 | Yarosh |

(Continued)

FOREIGN PATENT DOCUMENTS

| | | |
|---|---|---|
| CN | 103181933 (A) | 7/2013 |
| CN | 103184246 (A) | 7/2013 |

(Continued)

OTHER PUBLICATIONS

Tanret et al., 1909, caplus an 1909:14606.*
Altman, et al., 1985, "Ring Opening of N-Tosylhistamine with Di-t-butyl Pyrocarbonate: Synthesis of 1,2 Diamino-4-tosylaminobutane Dihydrochloride," J. Chem. Soc., Chem. Comm., pp. 1133-1134.
Altman, et al., 1990, "Approach to Chiral Vicinal Diacylamines by Bamberger Ring Cleavage of Substituted Imidazoles," Liebigs Ann. Chem., pp. 339-343.

(Continued)

*Primary Examiner* — Sun Jae Yoo

(74) *Attorney, Agent, or Firm* — Squire Patton Boggs (US) LLP

(57) ABSTRACT

Provided herein are $N^\alpha,N^\alpha,N^\alpha$-trialkyl histidine derivative compounds and methods of their preparation. Also provided are methods of their use for preparing useful compounds such as ergothioneine.

16 Claims, No Drawings

(56) References Cited

U.S. PATENT DOCUMENTS

| | | |
|---|---|---|
| 2015/0157648 A1 | 6/2015 | Hausman |
| 2015/0225755 A1 | 8/2015 | Liu et al. |

FOREIGN PATENT DOCUMENTS

| | | |
|---|---|---|
| CN | 103734022 (A) | 4/2014 |
| CN | 103743825 (A) | 4/2014 |
| JP | 2011050350 | 3/2011 |
| WO | WO 2013/101713 A1 | 7/2013 |
| WO | WO 2013/149258 A2 | 10/2013 |
| WO | WO 2013/149323 A1 | 10/2013 |
| WO | WO 2014/004647 A1 | 1/2014 |
| WO | WO 2014/043230 A2 | 3/2014 |
| WO | WO 2014/060233 A1 | 4/2014 |
| WO | WO 2014/071354 | 5/2014 |
| WO | WO 2014/089431 A1 | 6/2014 |
| WO | WO 2014/100752 A1 | 6/2014 |
| WO | WO 2014/182917 | 11/2014 |
| WO | WO 2015/030702 | 3/2015 |

OTHER PUBLICATIONS

Ashley, et al., 1930, "Synthesis of 1-2-Thiolhistidine", J. Chem. Soc., pp. 2586-2590.

Bamberger, E. 1893, "Studien uber Imidazole," Liebigs Ann. Chem. 273, pp. 342-363.

Cheah, et al., 2011, "Ergothioneine; antioxidant potential, physiological function and role in disease," Biochim. Biophys. Acta, doi = 10.1016/j.bbadis.2011.09.017.

Grace, et al., 1980, "Kinetics and Mechanism of the Bamberger Cleavage of Imidazole and of Histidine Derivatives by Diethyl Pyrocarbonate in Aqueous Solution," J. Am. Chem. Soc., vol. 102, pp. 6784-6789.

Heath, et al., 1950, "Synthesis of Ergothioneine," Nature, No. 4211, vol. 166, pp. 106.

International Search Report and Written Opinion for PCT/US2016/021992, dated Jun. 2, 2016, 10 pages.

Ishikawa, et al., 1974, "Participation of an Intermediate Sulfoxide in the Enzymatic Thiolation of the Imidazole Ring of Hercynine to Form Ergothioneine," J. Biol. Chem. vol. 249, pp. 4420-4427.

Ito, Shosuke, 1985, "Synthesis of 2-S-Cysteinylhistidine and 2-Mercaptohistidine via Bromo Lactone Derivative of Histidine," J. Org. Chem. vol. 50, pp. 3636-3638.

Khonde, et al. 2015, "Improved synthesis of the super antioxidant, ergothioneine, and its biosynthetic pathway intermediates," Org. Biomol. Chem. vol. 13, pp. 1415-1419.

Khonde, et al., 2015, Supporting information for "Improved synthesis of the super antioxidant, ergothioneine, and its biosynthetic pathway intermediates," Org. Biomol. Chem. vol. 13, pp. 1415-1419, (41 pages).

National Center for Biotechnology Information, Pubchem Entry CID 7408399: AC1OLRAH, created Jul. 2006, last modified Apr. 23, 2016, 11 pages [Retrieved on Apr. 28, 2016]. Retrieved from the Internet <URL: https://pubchem.ncbi.nlm.nih.gov/compound/7408399>.

Pratt, et al., 1981, "Ring Opening and Closing Reactions of Imidazoles and Other 1, 3 Diazaheterocycles with Vinyl Chloroformate and Phenyl Chloroformate," Tetrahedron Letters, vol. 22, No. 26, pp. 2431-2434.

Sata et al., 1999, "Answer 1 of 1 Caplus Copyright 2016 ACS on STN," Tetrahedron Letters, 40(4), pp. 719-722.

Xu, et al., 1995, "Sythesis of L-(+)-Ergothioneine," J. Org. Chem. vol. 60, pp. 6296-6301.

* cited by examiner

$N^\alpha, N^\alpha, N^\alpha$-TRIALKYL HISTIDINE DERIVATIVES USEFUL FOR THE PREPARATION OF ERGOTHIONEINE COMPOUNDS

CROSS-REFERENCE TO RELATED APPLICATIONS

This application is a continuation of U.S. application Ser. No. 15/067,687, entitled "$N^\alpha,N^\alpha,N^\alpha$-Trialkyl Histidine Derivatives Useful For The Preparation Of Ergothioneine Compounds," filed Mar. 11, 2016, which in turn claims priority to U.S. Application No. 62/133,165, entitled "$N^\alpha$, $N^\alpha,N^\alpha$-Trialkyl Histidine Derivatives Useful For The Preparation Of Ergothioneine Compounds," filed Mar. 13, 2015, and to U.S. Application No. 62/173,895, entitled "$N^\alpha,N^\alpha$, $N^\alpha$-Trialkyl Histidine Derivatives Useful For The Preparation Of Ergothioneine Compounds," filed Jun. 10, 2015. The contents of each of the foregoing applications are incorporated by reference herein in their entirety as if put forth fully below.

FIELD

Provided herein are compounds and methods useful for the preparation of certain betaines such as ergothioneine. Also provided herein are methods of preparing the compounds and methods of their use for the preparation of certain betaines such as ergothioneine.

BACKGROUND

Ergothioneine was discovered at the beginning of the 20th century in an ergot fungus contaminant of rye. Tenret, 1909, *Comp. Rend. Acad. Sci.* 149:222-224. The compound ergothioneine has been shown to protect cells from reactive oxidative species in bacteria, fungi, plants, and animals, including humans. Paul & Snyder, 2010, *Cell Death Differ.* 17:1134-1140; Emani et al., 2013, *Antimicrob. Agents Chemother.* 57:3202-3207. However, only certain bacteria and certain fungi have been shown to produce the compound themselves. Fahey, 2001, *Annu. Rev. Microbiol.* 55:333-356. Plants acquire ergothioneine from microbes in the soil. Audley & Tan, 1968, *Phytochemistry* 7:1999-2000. Animals, including humans, absorb ergothioneine from their diet. Humans have a specific transporter, ETT, for the uptake of ergothioneine. Gründemann et al., 22005012, *Proc. Natl. Acad. Sci. USA* 102:5256-5261. Cells that express ETT accumulate and retain ergothioneine at high levels. Id. The compound has a long biological half-life in the cell. Wolf et al., 1961, *Biochem. Biophys. Acta* 54:287-293. It is believed that ergothioneine provides antioxidant cytoprotection in such cells. Paul & Snyder, supra.

To date, ergothioneine has been proposed and used in several human and animal products. These include use as a skin toner additive (U.S. Pat. No. 7,122,211), as a photoprotective agent for human skin (U.S. Pat. No. 7,022,317), for the amelioration of liver disease (U.S. Pat. No. 6,555,141), for preventing diseases associated with oxidative damage to mitochondria (U.S. Pat. No. 6,479,533; U.S. Pat. No. 6,103,746), for repair of skin connective tissue damage (U.S. Pat. No. 6,451,771), and for other pharmaceutical antioxidant uses (U.S. Pat. No. 6,326,034; U.S. Pat. No. 6,056,965).

However, synthesis of ergothioneine has proved difficult and expensive. Commercial sources of ergothioneine can cost tens of thousands of dollars per gram. Prior syntheses of ergothioneine have involved many steps, challenging yields, and potentially toxic reagents. See, e.g., U.S. Pat. Nos. 5,438,151, 7,767,826, and 8,399,500. Improved methods for preparing ergothioneine on an industrial scale are needed.

SUMMARY

Provided herein are $N^\alpha,N^\alpha,N^\alpha$-trialkyl histidine derivative compounds and methods for their preparation. Also provided herein are methods of using the $N^\alpha,N^\alpha,N^\alpha$-trialkyl histidine derivative compounds for the preparation of certain betaines such as ergothioneine. Ergothioneine is useful for protecting cells from reactive oxidative species in plants and animals, including humans.

In one aspect, provided herein are methods for the preparation of a compound according to Formula 3:

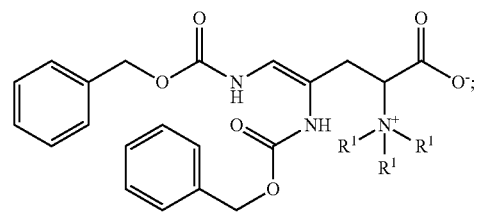

or a salt thereof. In Formula 3, each $R^1$ can be $(C_{1-4})$alkyl. In the methods, the starting material is a compound according to Formula 1:

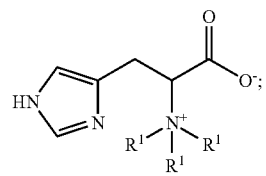

or a salt or tautomer thereof. In Formula 1, each $R^1$ can be $(C_{1-4})$alkyl. In particular embodiments, the compound of Formula 1 is hercynine (i.e. [(1S)-1-carboxy-2-(1H-imidazol-5-yl)ethyl]-trimethylazanium). In the methods, the compound according to Formula 1 is reacted with a chloroformate of formula (benzyl)-OC(O)X where X is halo to open the imidazole ring and yield the compound of Formula 3. Those of skill in the art will recognize that the methods use the Bamberger imidazole cleavage reaction. Certain methods provided herein are based at least in part on the discovery that the Bamberger imidazole cleavage reaction can be applied to a quaternary amine according to Formula 1 without resulting in racemization.

In another aspect, provided herein are methods for the preparation of a compound according to Formula 4:

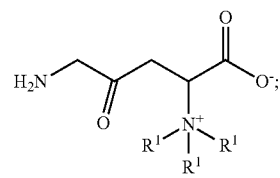

or a salt thereof. In Formula 4, each R[1] can be (C$_{1-4}$)alkyl. In the methods, the starting material is a compound according to Formula 3, above, or a salt thereof. In one embodiment, the compound according to Formula 3 is transformed by hydrogenolysis using a catalyst, such as Pd/C, and hydrogen gas to yield the compound of Formula 4. In another embodiment, the compound of Formula 3 is transformed to a compound of Formula 4 by hydrolysis and rearrangement with an acid, for example, a mineral acid such as hydrochloric acid.

In another aspect, provided herein are methods for the preparation of a compound according to Formula 5:

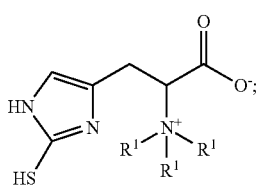

5 or a salt or tautomer thereof. In Formula 5, each R[1] can be (C$_{1-4}$)alkyl. In particular embodiments, the compound of Formula 5 is ergothioneine. In the methods, the starting material is a compound according to Formula 4, above, or a salt thereof. In the methods, the compound according to Formula 4 is reacted with a thiocyanate to yield the compound of Formula 5.

In another aspect, provided herein are compounds according to Formula 3:

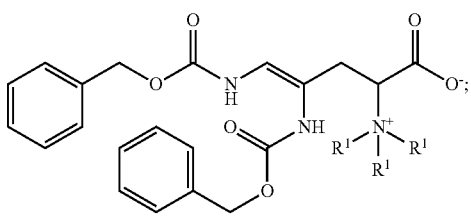

3 and salts thereof. In Formula 3, each R[1] can be (C$_{1-4}$)alkyl. Compounds of Formula 3 are useful, for example, for the preparation of certain betaines such as ergothioneine.

The above methods provide a robust three-step synthesis of compounds such as ergothioneine from starting materials such as hercynine which is easily obtained using methods known in the art (e.g., Reinhold et al., "Synthesis of α-N-methylated Histidines," *J. Med. Chem.* 1968, 11(2), pp. 258-260). In addition, the methods provided can be done on an industrial scale. In one embodiment, the reactions can be done at high volumes and in another embodiment the reactions can be scaled to 100,000 L or more.

DESCRIPTION OF EXEMPLARY EMBODIMENTS

Provided herein are methods of making N$^{\alpha}$,N$^{\alpha a}$,N$^{\alpha}$-trialkyl histidine derivative compounds, and methods of their use for making compounds such as ergothioneine. Ergothioneine is useful for protecting cells from reactive oxidative species in microbes, plants, and animals, including humans.

Definitions

When referring to the methods and compounds described herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, in another embodiment one to four carbon atoms. In certain embodiments, the alkyl group is selected from the group consisting of methyl, ethyl, propyl, isopropyl, butyl, isobutyl, sec-butyl, and t-butyl. The term includes both substituted and unsubstituted alkyl groups, including halogenated alkyl groups. In certain embodiments, the alkyl group is a fluorinated alkyl group. In certain embodiments, the alkyl group can be substituted with at least one (in certain embodiments 1, 2, 3, 4, or 5) group selected from the group consisting of halogen (fluoro, chloro, bromo or iodo), hydroxyl, alkylcarbonyl, cycloalkylcarbonyl, arylcarbonyl, cycloalkyl, aryl, sulfanyl, alkylsulfanyl, cycloalkylsulfanyl, arylsulfanyl, amino (as defined herein, e.g., alkylamino, arylamino etc.), alkoxy, aryloxy, nitro, cyano, sulfonic acid, sulfate, sulfonate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. In certain embodiments, the alkyl group can be substituted with 1, 2, 3, 4, or 5 or more substituents described above. In certain embodiments, the alkyl group is unsubstituted.

The term "alkoxy" as used herein refers to an —OR group where R is alkyl as defined herein. In certain embodiments, alkoxy and alkoxyl groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkylcarbonyl" as used herein refers to a —C(O)R group where R is alkyl as defined herein.

The term "alkylsulfanyl" as used herein refers to a —SR group where R is alkyl as defined herein.

"Amino" refers to the group —NRR' wherein R and R' are independently hydrogen, alkyl, alkenyl, alkynyl, cycloalkyl, heterocyclic, aryl, or heteroaryl, each of which is as defined herein. In an embodiment, "amino" is —NH$_2$.

The term "aryl," as used herein, and unless otherwise specified, refers to a substituent derived from a carbocyclic aromatic ring. In an embodiment, an aryl group is a C$_6$-C$_{12}$ aryl group. In an embodiment, an aryl group is phenyl or naphthyl. The term includes both substituted and unsubstituted moieties. An aryl group can be substituted with one or more moieties (in certain embodiments 1, 2, 3, 4, or 5) independently selected from the group consisting of halogen (fluoro, chloro, bromo or iodo), alkyl, haloalkyl, hydroxyl, amino (as defined herein, e.g. alkylamino, arylamino etc.), alkoxy, aryloxy, nitro, cyano, sulfonic acid, sulfate, sulfonate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991. In certain embodiments, an aryl group is substituted with 1, 2, 3, 4, 5, or more moieties described above.

The term "aralkyl" as used herein refers to an alkyl group substituted with one or two aryl groups.

The term "arylcarbonyl" as used herein refers to a —C(O)R group where R is aryl as defined herein.

The term "aryloxy" as used herein refers to a —OR group where R is aryl as defined herein.

The term "arylsulfanyl" as used herein refers to an —SR group where R is aryl as defined herein.

The term "cycloalkyl," as used herein, unless otherwise specified, refers to a saturated monocyclic or polycyclic hydrocarbon. In certain embodiments, cycloalkyl includes fused, bridged, and spiro ring systems. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is, for example, cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl.

The term "cycloalkylcarbonyl" as used herein refers to a —C(O)R group where R is cycloalkyl as defined herein.

The term "cycloalkylsulfanyl" as used herein refers to a —SR group where R is cycloalkyl as defined herein.

The term "phosphonic acid" refers to —P(O)(OH)$_2$.

The term "phosphate" refers to the group —OP(O)(OR)$_2$ where each R is independently alkyl or arylalkyl.

The term "phosphonate" refers to the group —P(O)(OR)$_2$ where each R is independently alkyl or arylalkyl.

The term "sulfanyl" as used herein refers to a —SH group.

The term "sulfonic acid" refers to the group —S(O)$_2$OH.

The term "sulfate" refers to the group —OS(O)$_2$OR where R is alkyl or arylalkyl.

The term "sulfonate" refers to the group —S(O)$_2$OR where R is alkyl or arylalkyl.

"Salt" refers to any salt of a compound provided herein. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

In certain embodiments, the salt of a compound provided herein retains its biological properties and is not toxic or otherwise undesirable for pharmaceutical use.

The term "substantially free of" or "substantially in the absence of" with respect to a composition refers to a composition that includes at least about 85 or 90% by weight, in certain embodiments at least about 95%, 98%, 99% or 100% by weight, of a designated enantiomer or stereoisomer of a compound. For example, "substantially free of" or "substantially in the absence of" with respect to a composition can refer to a composition that includes about 85%, 86%, 87%, 88%, 89%, 90%, 91%, 92%, 93%, 94%, 95%, 96%, 97%, 98%, 99%, or 100% by weight of a designated enantiomer or stereoisomer of a compound. In certain embodiments, in the methods and compounds provided herein, the compounds are substantially free of other enantiomers or stereoisomers.

Similarly, the term "isolated" with respect to a composition refers to a composition that includes at least 85, 90%, 95%, 98%, 99% to 100% by weight, of a designated compound, enantiomer, or stereoisomer, the remainder comprising other chemical species, enantiomers, or stereoisomers. For example, "isolated" with respect to a composition can refer to a composition that includes about 85%, 86%, 87%, 88%, 89%, 90%, 91%, 92%, 93%, 94%, 95%, 96%, 97%, 98%, 99%, or 100% by weight of a designated compound, enantiomer, or stereoisomer, the remainder comprising other chemical species, enantiomers, or stereoisomers.

Methods

Provided herein are methods of making $N^\alpha,N^\alpha,N^\alpha$-trialkyl histidine derivative compounds, and methods of their use for making compounds such as ergothioneine. Ergothioneine is useful for protecting cells from reactive oxidative species in microbes, plants, and animals, including humans.

The methods comprise any or all of steps (a), (b), and (c), below. In some embodiments, the methods comprise step (a). In some embodiments, the methods comprise step (b). In some embodiments, the methods comprise step (c). In some embodiments, the methods comprise step (a) and step (b). In some embodiments, the methods comprise step (b) and step (c). In some embodiments, the methods comprise steps (a), (b) and (c).

In one aspect, provided herein are methods comprising step (a). In step (a), a $N^\alpha,N^\alpha,N^\alpha$-trialkyl histidine derivative compound is reacted with an acyl chloride or a chloroformate to open its ring:

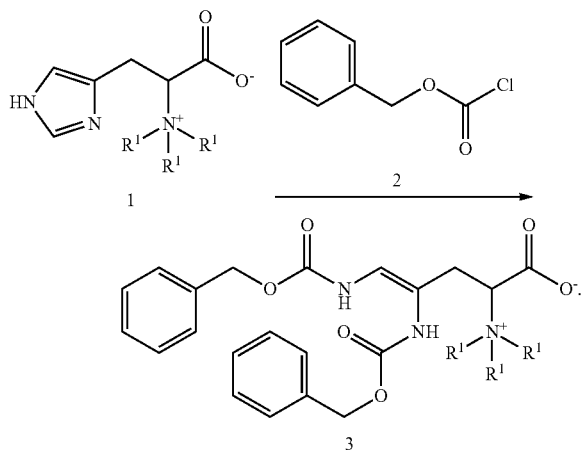

In Formula 1, each $R^1$ is $(C_{1-4})$alkyl. The $R^1$ alkyl groups can be the same or different. In particular embodiments, the alkyl groups are the same. In particular embodiments, each $R^1$ is methyl. In Formula 3, each $R^1$ is consistent with Formula 1. Preferably, in Formula 1, and Formula 3, each $R^1$ is unsubstituted.

In step (a), the reaction is carried out one or more solvents. In certain embodiments, the mixture of solvents is a biphasic system consisting of water and another solvent not completely miscible with water. The solvent(s) can be any solvent deemed suitable to those of skill in the art for carrying out the reaction. In certain embodiments, the solvent(s) is partially miscible with water and does not appreciably react with the compound of Formula 2. In certain embodiments, the solvent(s) is selected from the group consisting of water, ethyl acetate, tetrahydrofuran (THF), 2-methyltetrahydrofuran, dioxane, methyl ethyl ketone, acetone, dimethylformamide, dimethylsulfoxide, diglyme, (bis)-methoxymethyl ether, and (bis)-2-ethoxyethyl ether. In particular embodiments, the solvent is a mixture of THF and water. For, instance, the solvent can be 50% THF and 50% water. In particular embodiments, the solvent is ethyl acetate. In certain embodiments, the solvent(s) is selected from the group consisting of water, ethyl acetate, tetrahydrofuran (THF), 2-methyltetrahydrofuran, dioxane, methyl ethyl ketone, acetone, dimethylformamide, diethyl ether, dimethylsulfoxide, diglyme, (bis)-methoxymethyl ether, and (bis)-2-ethoxyethyl ether. In particular embodiments, the solvent is a mixture of diethyl ether and water. In some embodiments, the solvent is 50% diethyl ether and 50% water. In particular embodiments, the solvent is ethyl acetate or THF.

The reaction of step (a) is preferably carried out with a base. In particular embodiments, the base is selected from the group consisting of sodium bicarbonate, sodium carbonate, potassium acetate, sodium hydroxide, sodium acetate, and potassium hydrogen carbonate. In particular embodiments, the base is bicarbonate, for example sodium bicarbonate.

The concentration of the compound according to Formula 1 is about 0.05M to about 1.2M, in another embodiment about 0.1M in another embodiment about 0.2M in another embodiment about 0.3M in another embodiment about 0.4M in another embodiment about 0.5M in another embodiment about 0.6M in another embodiment about 0.7M in another embodiment about 0.8M, in another embodiment about 0.9M in another embodiment about 1.0M in another embodiment about 1.1M, and in another embodiment about 1.2M. The compound according to Formula 2 is used in an amount of at least about 2 equivalents with respect to the compound of Formula I, and in some embodiments about 2 equivalents, about 2.5 equivalents, about 3 equivalents, or about 3.5 equivalents. In particular embodiments, the compound of Formula 2 is in at least a two-fold molar excess compared to the compound of Formula 1.

The reaction of step (a) is carried out at any temperature deemed suitable by those of skill in the art. In particular embodiments, the reaction is conducted at any temperature from about 0° C. to about 30° C., from about 5° C. to about 25° C., from about 10° C. to about 25° C., from about 18° C. to about 25° C., or from about 20° C. to about 30° C. In particular embodiments, the reaction is at room temperature. In particular embodiments, the reaction is conducted at about 20° C., about 21° C., about 22° C., about 23° C., about 24° C., or about 25° C.

The reaction of step (a) can be carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is from at least about 200 mL to at least about 100,000 L. In another embodiment, the reaction volume is at least about 1000 L, at least about 5000 L, at least about 10,000 L, at least about 25,000 L, at least about 50,000 L, at least about 75,000 L, or at least about 100,000 L.

The reaction of step (a) can proceed for any time deemed suitable for formation of the compound according to Formula 3. In particular embodiments, the reaction proceeds for about 1-48 hours. In particular embodiments, the reaction proceeds for about 1-8 hours, in another embodiment about 1-5 hours, in another embodiment about 2-12 hours, and in another embodiment about 5-48 hours. In certain embodiments, the reaction proceeds for about 15-30 hours. In particular embodiments, the reaction proceeds for about 24 hours. In certain embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography.

In certain embodiments, the compound of Formula 3 is isolated from the reaction mixture. The compound can be isolated by any technique deemed suitable by those of skill. In particular embodiments, side products such as an alcohol can be removed by extraction with dichloromethane, ethyl acetate or ether.

In another aspect, provided herein are methods comprising step (b). One embodiment of step (b) is step (b)(1). In step (b)(1), a ring-opened compound of Formula 3 is treated with a catalyst, such as Pd/C or Pd/C sulfided, and hydrogen gas:

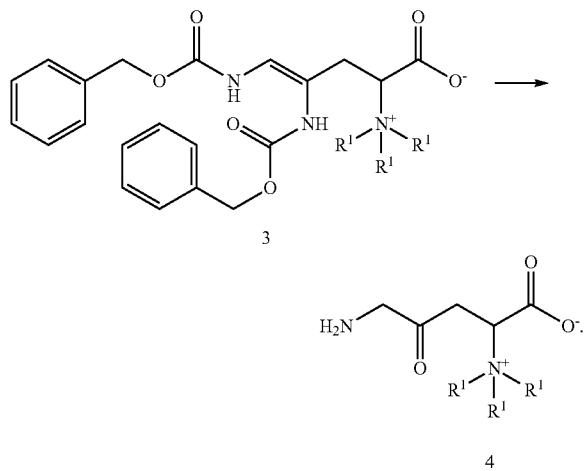

In Formula 3, each $R^1$ is $(C_{1-4})$alkyl. The $R^1$ alkyl groups can be the same or different. In particular embodiments, the alkyl groups are the same. In particular embodiments, each $R^1$ is methyl. In Formula 4, each $R^1$ is consistent with Formula 3. Preferably, in Formula 3 and Formula 4, each $R^1$ is unsubstituted.

The reaction of step (b)(1) is carried out using a catalyst and hydrogen gas or alternatively, formic acid, ammonium formate, cyclohexene, cyclohexadiene or the like. The catalyst can be any deemed suitable by those of skill. In particular embodiments, the catalyst is a Palladium catalyst (e.g. Pd/C, Pd/C sulfided, a Lindlar catalyst), a Rhodium catalyst (e.g. Wilkinson's catalyst), a Nickel catalyst (e.g. Raney Nickel, Urushibara Nickel), or a Pt catalyst. In some embodiments, the catalyst is Pd/C, Pd/C sulfided, Pd/CaSO$_4$, Pd/BaSO$_4$, Pd/CaCO$_3$, RhCl(PPh$_3$)$_3$, Raney Nickel, Pt/CaSO$_4$, Pt/BaSO$_4$, or Pt/CaCO$_3$; where the Pd/CaSO$_4$, Pd/BaSO$_4$, Pd/CaCO$_3$, Pt/CaSO$_4$, Pt/BaSO$_4$, and Pt/CaCO$_3$ catalysts are optionally partially poisoned (in one embodiment optionally partially poisoned with Pb or 2,6-lutidine). In particular embodiments, the catalyst is Pd/C or Pd/C sulfided. In some embodiments, the amount of catalyst employed to carry out the reaction is about 0.2 mol % to about 20 mol %, about 0.25 mol % to about 10 mol %, about 0.5 mol % to about 7.5 mol %, about 1 mol %, about 2 mol %, about 3 mol %, about 4 mol %, about 5 mol %, about 6 mol %, about 7 mol %, about 8 mol %, about 9 mol %, or about 10 mol %. In certain embodiments, the amount of catalyst is about 0.2 mol % to about 20 mol % Pd/C, about 0.25 mol % to about 10 mol % Pd/C, about 0.5 mol % to about 7.5 mol % Pd/C, about 1 mol % Pd/C, about 2 mol % Pd/C, about 3 mol % Pd/C, about 4 mol % Pd/C, about 5 mol % Pd/C, about 6 mol % Pd/C, about 7 mol % Pd/C, about 8 mol % Pd/C, about 9 mol % Pd/C, or about 10 mol % Pd/C.

In step (b)(1), the reaction is carried out in one or more solvent(s). The solvent(s) can be any solvent deemed suitable to those of skill in the art for carrying out the reaction. In certain embodiments, the solvent(s) is selected from the group consisting of dilute hydrochloric acid (in one embodiment about 1%), water, methanol, ethanol, and combinations thereof. In particular embodiments, the solvent is water.

In step (b)(1), the concentration of the compound according to Formula 3 is preferably from about 1 g/100 mL to about 10 g/100 mL, in another embodiment about 3 g/100 mL to about 6 g/100 mL, and in another embodiment about 4 g/100 mL to about 5 g/100 mL. In another embodiment, the concentration is about 1 g/100 mL, about 2 g/100 mL, about 3 g/100 mL, about 4 g/100 mL, about 5 g/100 mL, about 6 g/100 mL, about 7 g/100 mL, about 8 g/100 mL, about 9 g/100 mL, or about 10 g/100 mL. The amount of catalyst is preferably from about 0.25 mol % Pd/C to about 7.5 mol % Pd/C.

The reaction of step (b)(1) is carried out at any temperature deemed suitable by those of skill in the art. In particular embodiments, the reaction is conducted at any temperature from about 20° C. to about 30° C., from about 20° C. to about 28° C., or from about 20° C. to about 25° C. In particular embodiments, the reaction is at room temperature. In particular embodiments, the reaction is conducted at about 20° C., about 21° C., about 22° C., about 23° C., about 24° C., or about 25° C.

The reaction of step (b)(1) can be carried out in any volume deemed suitable by those of skill in the art. In particular embodiments, the reaction volume is at least about 500 mL, at least about 1 L, at least about 2 L, at least about 3 L, at least about 4 L, or at least about 5 L. In another embodiment, the reaction volume is from at least about 500 mL to at least about 100,000 L. In another embodiment, the reaction volume is at least about 1000 L, at least about 5000 L, at least about 10,000 L, at least about 25,000 L, at least about 50,000 L, at least about 75,000 L, or at least about 100,000 L.

The reaction of step (b)(1) can proceed for any time deemed suitable for formation of the compound according to Formula 4. In particular embodiments, the reaction proceeds for about 1 hour, about 2 hours, about 3 hours, about 4 hours, about 5 hours, about 6 hours, or about 7 hours. In particular embodiments, the reaction proceeds for about 1 to about 6 hours, in another embodiment about 3 to about 6 hours. Reaction progress can be monitored by standard techniques such as thin layer chromatography or high-performance liquid chromatography.

Another embodiment of step (b) is step (b)(2). In Step (b)(2), a ring-opened compound of Formula 3 is transformed to a to compound of Formula 4 by hydrolysis and rearrangement using an acid. The acid can be any acid deemed useful by the practitioner of skill. Useful acids include hydrochloric acid, nitric acid, phosphoric acid, sulfuric acid, boric acid, hydrofluoric acid, hydrobromic acid, and trifluoroacetic acid.

In step (b)(2), the concentration of the compound according to Formula 3 can be any concentration deemed useful by the practitioner of skill. In certain embodiments, the concentration is at least about 1 g/10 mL. In certain embodiments, the concentration is from about 1 g/10 mL to about 1 g/mL, or from about 1 g/10 mL to about 5 g/10 mL, or from about 1 g/10 mL to about 3 g/10 mL. In particular embodiments, the concentration is about 1 g/10 mL, 2 g/10 mL, 3 g/10 mL, 4 g/10 mL, or 5 g/10 mL, 6 g/10 mL, 7, g/10 mL, 8 g/10 mL, 9 g/10 mL or 1 g/mL.

In step (b)(2), the concentration of acid is any amount deemed sufficient for the hydrolysis and rearrangement to proceed. In certain embodiments, the acid concentration is from about 1% to about 38% (w/v). In certain embodiments, the acid concentration is from about 5% to about 38% (w/v), or from about 10% to about 38% (w/v), from about 15% to about 38% (w/v), or from about 20% to about 38% (w/v). In certain embodiments, the acid concentration is from about 20% to about 38% (w/v). The acid can be in any solvent deemed suitable, for instance, water. In particular embodiments, the reaction proceeds in aqueous acid. In certain embodiments, the reaction proceeds in aqueous acid with an immiscible solvent. The immiscible solvent can advantageously extract the benzyl chloride side product. Useful immiscible solvents include ethyl acetate, ether, dichloromethane, and the like. The ratio of immiscible solvent to aqueous solution can be any ratio deemed suitable. In some embodiments, the ratio of immiscible solvent to aqueous solution can be from about 1:10 to about 10:1, or from about 1:5 to about 5:1, or from about 1:3 to about 3:1, or from about 1:2 to about 2:1, or about 1:1. In some embodiments, the ratio is about 3:10 immiscible solvent to aqueous solution. The reaction volume can be any volume deemed useful by the practitioner of skill. In certain embodiments, the reaction volume can range from 25 mL to 40 L or greater. In certain embodiments, the reaction volume is at least about 25 mL, 50 mL, 100 mL, 250 mL, 500 mL, 1 L, 2 L, 5 L, 10 L, 20 L, 25 L, 30 L, 35 L, or 40 L.

In step (b)(2), the reaction can be carried out at any temperature deemed suitable by those of skill in the art. In certain embodiments, the reaction is carried out at a temperature of about 0° C. to about 40° C. In certain embodiments, the reaction is carried out at a temperature of about 5° C. to about 35° C. In certain embodiments, the reaction is carried out at a temperature of about 10° C. to about 30° C. In another embodiment, the reaction is carried out at a temperature of about 15° C. to about 25° C.

In step (b)(2), the reaction can proceed for any time deemed suitable for formation of the compound according to Formula 4. In certain embodiments, the time for reaction is from 24 hours to about 48 hours. In certain embodiments, the time for reaction is from about 1 hour to about 24 hours. In certain embodiments, the time for reaction is from 12 hours to about 24 hours. In certain embodiments, the time for reaction is from 12 hours to about 18 hours. In certain embodiments, the time for reaction is from 3 hours to about 15 hours. In certain embodiments, the time for reaction is from 8 hours to about 12 hours.

In certain embodiments, the compound of Formula 4 is isolated from the reaction mixture. The compound can be isolated by any technique deemed suitable by those of skill. In particular embodiments, the compound of Formula 4 is isolated by filtration and evaporation. In particular embodiments, the intermediate is used in the next step without further isolation or concentration. In further embodiments, the compound of Formula 4 is isolated by evaporation and optional filtration, followed by dissolving in a solvent for step (c) below. As described below, the useful solvents include hydrochloric acid in water or ethanol, or both.

In another aspect, provided herein are methods comprising step (c). In step (c), a compound of Formula 4 is reacted with a thiocyanate to yield the product according to Formula 5:

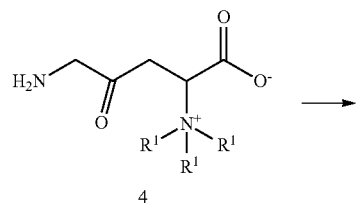

4

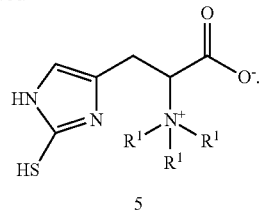

5

In Formula 4, each $R^1$ is $(C_{1-4})$alkyl. The $R^1$ alkyl groups can be the same or different. In particular embodiments, the alkyl groups are the same. In particular groups, each $R^1$ is methyl. In Formula 5, each $R^1$ is consistent with Formula 4. Preferably, in Formula 4 and Formula 5, each $R^1$ is unsubstituted.

The reaction of step (c) is carried out with a thiocyanate. The thiocyanate can be any thiocyanate deemed suitable by those of skill. In particular embodiments, the agent is selected from the group consisting of potassium thiocyanate (KCNS), lithium thiocyanate (LiCNS), ammonium thiocyanate ($NH_4CNS$), and sodium thiocyanate (NaCNS). In particular embodiments, the thiocyanate is KCNS. In particular embodiments, the thiocyanate is ammonium thiocyanate ($NH_4CNS$).

In step (c), the reaction is carried out in one or more solvent(s). The solvent(s) can be any solvent deemed suitable to those of skill in the art for carrying out the reaction. In certain embodiments, the solvent(s) is dilute hydrochloric acid (in one embodiment about 1% (w/v)) and water. In certain embodiments, the solvent(s) is hydrochloric acid (in certain embodiments from about 1% (w/v) to about 38% (w/v)) and water or ethanol, or both. In certain embodiments, the solvent(s) is water, 1-38% (w/v) hydrochloric acid, methanol, ethanol, isopropanol, or a combination thereof. In particular embodiments, the solvent is water.

The concentration of the compound according to Formula 4 is from about 0.5 g/25 mL to about 5 g/25 mL, in another embodiment from about 1 g/25 mL to about 4 g/25 mL. The amount of thiocyanate can be any amount deemed suitable by the practitioner of skill. In certain embodiments, the amount of thiocyanate is from about 1 to about 3 equivalents, relative to the amount of the compound of Formula 4. In certain embodiments, the amount of thiocyanate is from about 1 g/25 mL to about 5 g/25 mL. In particular embodiments, the amount of thiocyanate is about 1 g/5 mL. In some embodiments, the amount of thiocyanate is about 0.5 g/25 mL, 1 g/25 mL, 2 g/25 mL, 3 g/25 mL, or 4 g/25 mL.

The reaction of step (c) is carried out at any temperature deemed suitable by those of skill in the art. In particular embodiments, the reaction is conducted at any temperature from about room temperature to about 95° C. or to about 100° C. In particular embodiments, the reaction is conducted at any temperature from about 40° C. to about 95° C. In particular embodiments, the reaction is conducted at any temperature from about 50° C. to about 95° C. In particular embodiments, the reaction is conducted at any temperature from about 60° C. to about 95° C. In particular embodiments, the reaction is conducted at any temperature from about 70° C. to about 95° C. In particular embodiments, the reaction is conducted at any temperature from about 80° C. to about 95° C. In particular embodiments, the reaction is conducted at any temperature from about 85° C. to about 95° C. In particular embodiments, the reaction is at any temperature from about 85° C. to about 90° C.

The reaction of step (c) can be carried out in any volume deemed suitable by those of skill in the art. In particular embodiments, the reaction volume is at least about 10 mL, at least 20 mL, at least 25 mL, at least 50 mL, at least 60 mL, at least 70 mL, at least 80 ml, at least 90 mL, or at least 100 mL. In another embodiment, the reaction volume is at least about 10 mL to at least about 100,000 L. In another embodiment, the reaction volume is at least about 1000 L, at least about 5000 L, at least about 10,000 L, at least about 25,000 L, at least about 50,000 L, at least about 75,000 L, or at least about 100,000 L.

The reaction of step (c) can proceed for any time deemed suitable for formation of the compound according to Formula 5. In particular embodiments, the reaction proceeds for about 0.5 hours, about 1 hour, about 1.5 hours, about 2 hours, about 2.5 hours, about 3 hours, about 3.5 hours, about 4 hours, about 5 hours, about 6 hour 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In particular embodiments, the reaction proceeds for about 0.5 to about 2 hours and in another embodiment from about 0.5 to about 1.5 hours. In particular embodiments, the reaction is conducted at low temperature (in another embodiment, at any temperature from about 20° C. to about 100° C., in another embodiment, at any temperature from about 20° C. to about 60° C., in another embodiment at about 20° C., in another embodiment at about room temperature, in another embodiment at about 30° C., in another embodiment at about 35° C., in another embodiment at about 40° C., in another embodiment at about 45° C., in another embodiment at about 50° C., in another embodiment at about 55° C., in another embodiment at about 60° C., and in another embodiment at 100° C.) and is allowed to proceed overnight or about 18-24 hours. Reaction progress can be monitored by standard techniques such as thin layer chromatography or high-performance liquid chromatography.

In certain embodiments, the compound of Formula 5 is isolated from the reaction mixture. The compound can be isolated by any technique deemed suitable by those of skill. In particular embodiments, the compound of Formula 5 is isolated by filtration and evaporation and crystallization.

The present disclosure encompasses methods that comprise any of steps (a), (b), and (c). In particular embodiments, provided herein are methods of making compounds according to Formula 5 by following steps (a), (b), and (c) above. In further embodiments, provided herein are methods of making compounds according to Formula 5, wherein each $R^1$ is methyl, by following steps (a), (b), and (c) above. In such embodiments, the compound according to Formula 1 is hercynine and the compound according to Formula 5 is ergothioneine.

The compounds of Formulas 1, 3, 4, and 5 each include a chiral center. The present specification encompasses methods using compounds with any stereochemistry at the chiral centers. In particular embodiments, the compounds are racemic. In particular embodiments, the compounds have D-stereochemistry. In preferred embodiments, the compounds have L-stereochemistry.

In particular embodiments, the methods of step (a) are carried out with a compound according to Formula 1a:

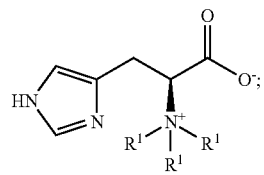

or a salt or tautomer thereof.

In particular embodiments, the methods of step (a) yield a compound according to Formula 3a:

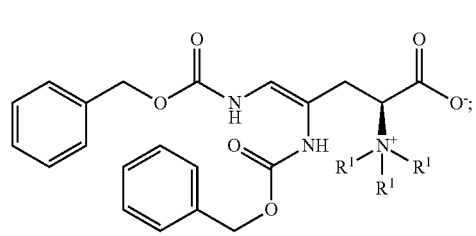

or a salt thereof.

In particular embodiments, the methods of step (b) are carried out with a compound according to Formula 3a:

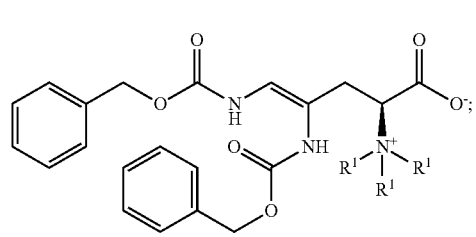

or a salt thereof.

In particular embodiments, the methods of step (b) yield a compound according to Formula 4a:

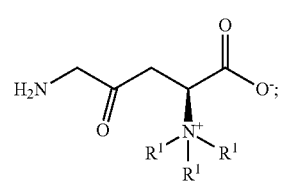

or a salt thereof.

In particular embodiments, the methods of step (c) are carried out with a compound according to Formula 4a:

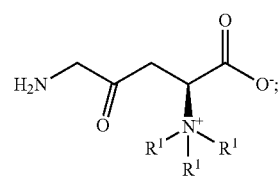

or a salt thereof.

In particular embodiments, the methods of step (c) yield a compound according to Formula 5a:

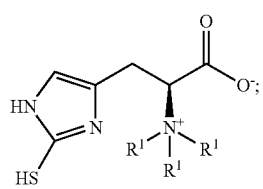

5a or a salt or tautomer thereof.

In particular embodiments, the methods of step (a) are carried out with a compound according to Formula 1b:

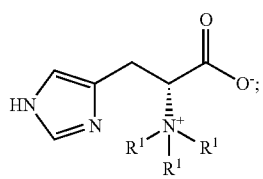

1b or a salt or tautomer thereof.

In particular embodiments, the methods of step (a) yield a compound according to Formula 3b:

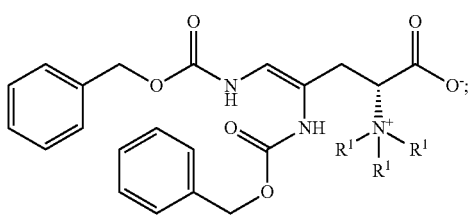

3b or a salt thereof.

In particular embodiments, the methods of step (b) are carried out with a compound according to Formula 3b:

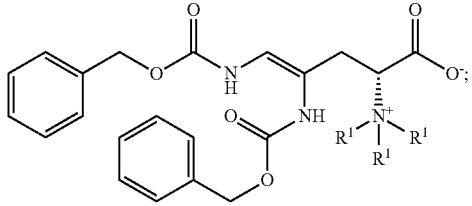

3b or a salt thereof.

In particular embodiments, the methods of step (b) yield a compound according to Formula 4b:

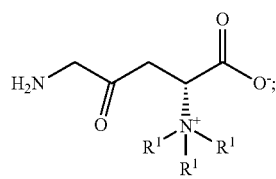

4b or a salt thereof.

In particular embodiments, the methods of step (c) are carried out with a compound according to Formula 4b:

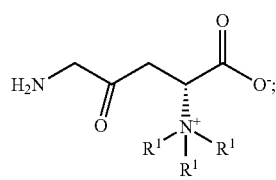

4b or a salt thereof.

In particular embodiments, the methods of step (c) yield a compound according to Formula 5b:

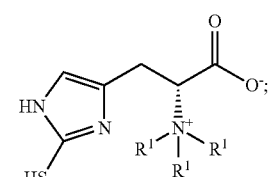

5b or a salt or tautomer thereof.

Compounds

Provided herein are compounds useful in the preparation of histidine derivatives such as ergothioneine. In certain embodiments, provided herein are compounds according to Formula 3:

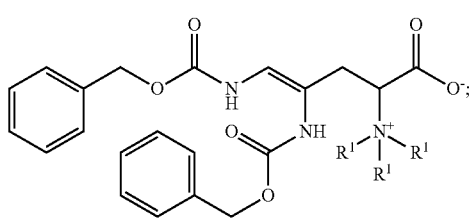

3 or salts thereof; wherein each $R^1$ is $(C_{1-4})$alkyl. In particular embodiments, the $(C_{1-4})$alkyl are unsubstituted. In particular embodiments, each $R^1$ is methyl.

Provided herein are compounds useful in the preparation of histidine derivatives such as ergothioneine. In certain embodiments, provided herein are compounds according to Formula 3a:

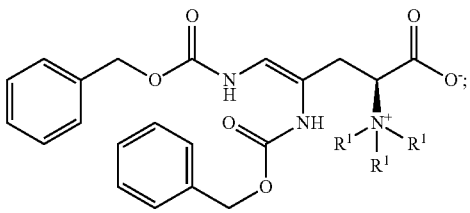

3a or salts thereof; wherein each $R^1$ is $(C_{1-4})$alkyl. In particular embodiments, the $(C_{1-4})$alkyl are unsubstituted. In particular embodiments, each $R^1$ is methyl.

Provided herein are compounds useful in the preparation of histidine derivatives such as ergothioneine. In certain embodiments, provided herein are compounds according to Formula 3b:

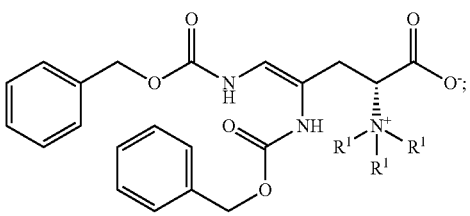

3b or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 4:

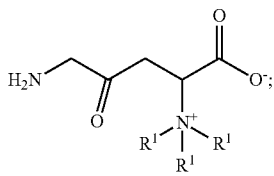

4 or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 4a:

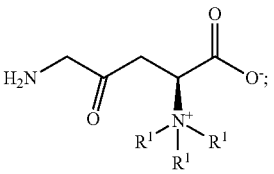

4a or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 4b:

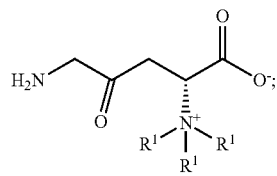

4b or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 5:

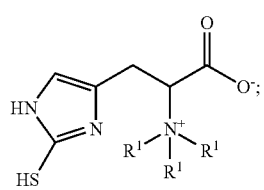

5 or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 5a:

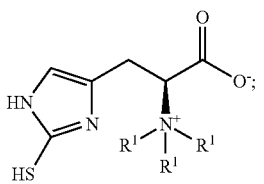

5a or salts thereof; wherein each $R^1$ is $(C_{1-4})$alkyl. In particular embodiments, the $(C_{1-4})$alkyl are unsubstituted. In particular embodiments, each $R^1$ is methyl.

In certain embodiments, provided herein are compounds according to Formula 5b:

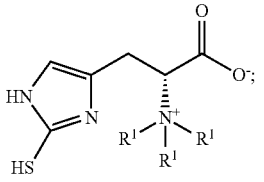

5b or salts thereof; wherein each $R^1$ is $(C_{1-4})$alkyl. In particular embodiments, the $(C_{1-4})$alkyl are unsubstituted. In particular embodiments, each $R^1$ is methyl.

Particular compounds include the following:

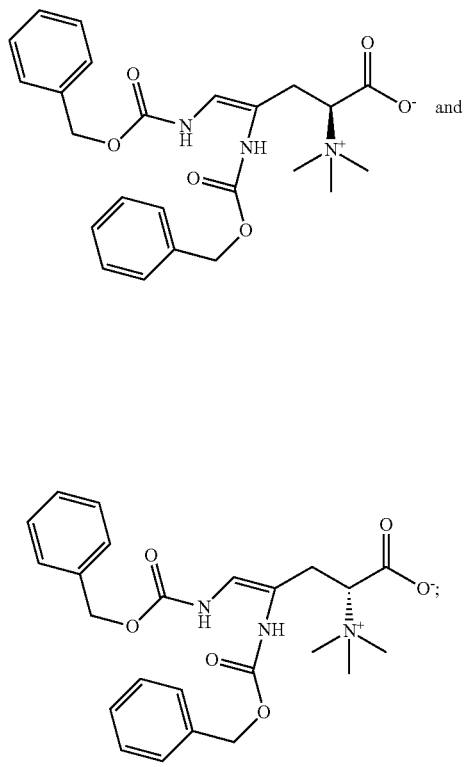

and salts thereof.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (or M, molar); mM (millimolar); µM (micromolar); Hz (Hertz); MHz (megahertz); mol (moles); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); RVE (rotary evaporator); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of L-Ergothioneine (E)

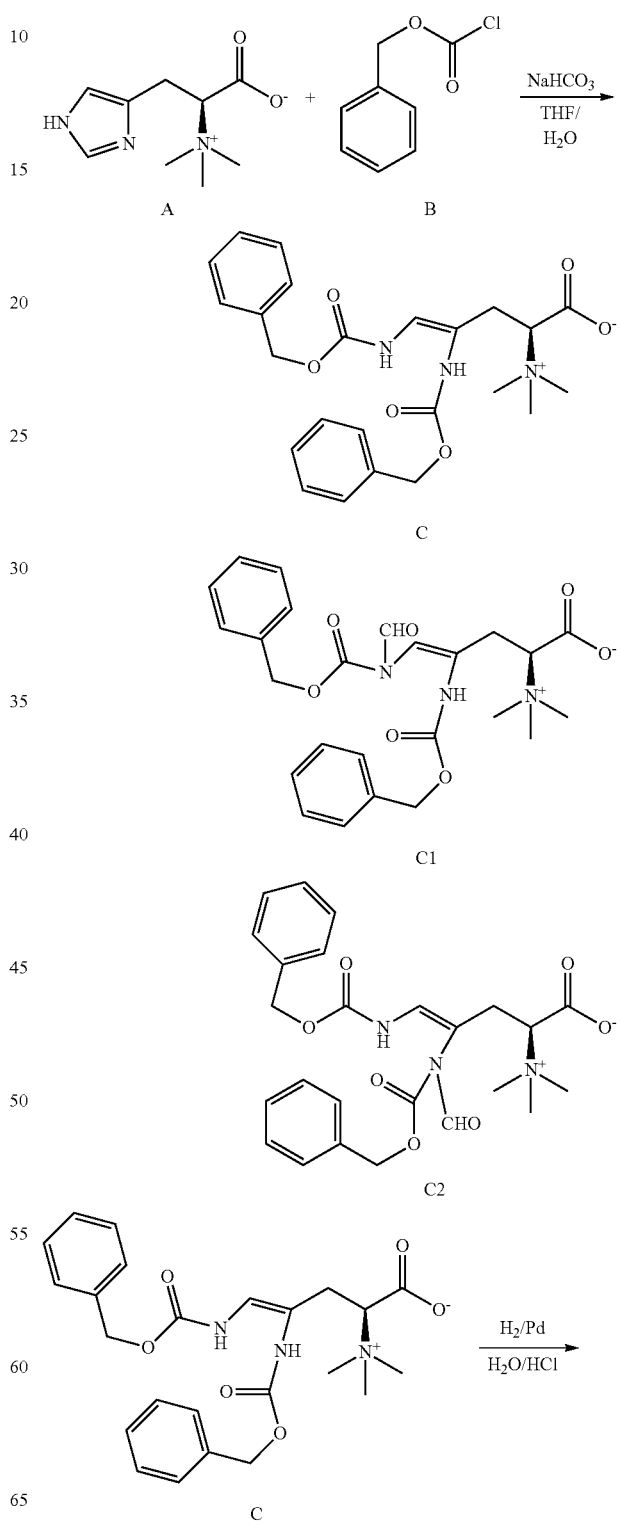

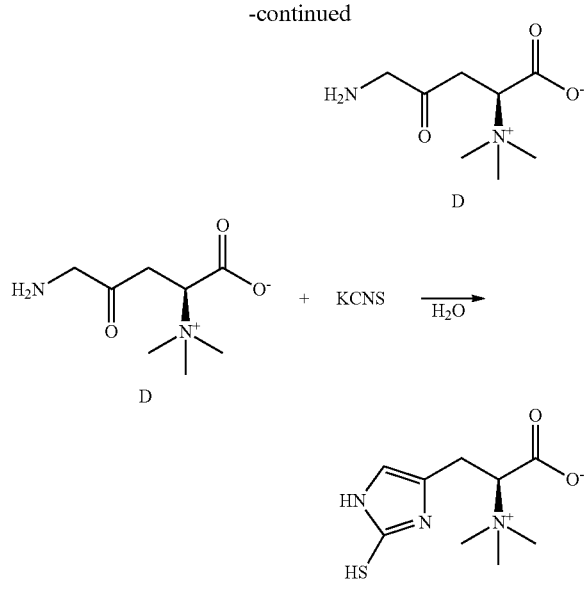

Compound C

To a 1 liter 3-neck flask with motor-stirrer, thermometer and 50 mL addition funnel was added 16 g (80 mmol) of hercynine (A), 300 mL water, 40 g (475 mmol) sodium bicarbonate and 300 mL THF. Under strong stirring was slowly added at room temperature over 15-20 minutes, drop wise, 30 mL (35.85 g, 210 mmol) CBZ-chloride (B).

After another 2 hours, a sample was analyzed by HPLC for the formation of product (C) in the form of C, C1 or C2, and little or no starting material (hercynine A or CBZ-chloride (B), or both). If starting materials remained, the reaction continued. When little or no starting material was present as analyzed by HPLC, small portions of dilute HCl were added to the mixture while stirring to achieve pH 4 to 5, and the contents of the reaction flask were transferred to a rotary evaporator flask.

Under vacuum and bath temperature 30° C., THF was removed and the rest in the flask (water) was transferred to a 1 liter separatory funnel. The side product—benzyl alcohol—was removed by extraction with ethyl acetate or ether.

After evaporation of the aqueous layer (RVE, 1 liter flask, 30° C. bath, vacuum) the oily residue was dissolved in methanol. After the insoluble material was removed by filtration. deformylation was carried out by heating for 2 hours at 64° C. (60-65° C.) in 500 mL of methanol on RVE. Reaction progress was checked by HPLC. When ready, the methanol was removed at 30-33° C. under vacuum to a constant weight. The residue was mixed with EtOH (200 mL) and evaporated to constant weight. The residue was stirred with 500 mL of DCM for 30 minutes at 30° C. and then filtered. The filtrate was evaporated and the product was recrystallized from IPA/ether After drying in open air compound C was produced as white to yellow crystals. Yield is 30 g (82%).

Compound D 5 g of compound C from step 1 was dissolved in 100 mL of 1% HCl. To this was added 0.1 g of 5% Pd/C Sulfided. To this solution/mixture under magnetic stirring in a 500 mL 3-neck flask was bubbled hydrogen gas until the evolution of $CO_2$ ceased, approximately 3 hours.

When reaction progress was complete by HPLC, the palladium was filtered off and the filtrate was used without purification in the next step.

The yield by weight is approximately 100%.

L-Ergothioneine (E)

The solution of compound D (approximately 11 mmol) from step 2 was warmed to 85-90° C. and 5 g of KCNS in 10 mL water was added. This solution was stirred in a water bath at 85-90° C. for 1-2 hours.

When reaction progress was complete by HPLC, this solution was cooled to approximately 30° C. Approximately 15 mL of concentrated HCl in 15 mL of water was added, and this acidic solution was evaporated (bath 30° C., vacuum). The residue was dissolved in 20 mL ethanol (200 proof) and was again evaporated. 30 mL ethanol (200 proof) was added. For a few minutes this mixture was stirred on bath at 30° C., and then cooled for 20 min on ice. The salts were filtered off and washed with 20 mL of ethanol (200 proof) and the filtrates were basified with a dilute solution of LiOH to pH 3.6-4 by pH meter.

After total evaporation under vacuum in order to remove water, the residue was stirred on RVE overnight with 30 mL ethanol. Then the solid was filtered, washed with 2×5 mL ethanol and dried. Approximately 0.8 g of solid crystalline L-ergothioneine was obtained. Analysis by HPLC showed approximately 85% pure product. Optical rotation was approximately 80-90°, and the color was light brown. From mother liquors, an additional 0.3 g was obtained, for a total 1.1 g (43%) of L-ergothioneine.

The yield of L-ergothioneine (E) from hercynine (A) is approximately 40-50%.

Example 2

Compound C

Example 2 proceeds according to Example 1 with the following exceptions. To obtain Compound C directly, with little or no C1 or C2, the reaction of A and B proceeds with stirring for 24-48 hours. The deformylation of C1 or C2 to C can proceed to completion or near completion. When by analysis the process is ready it is then acidified by dilute HCl to pH 4-5, transferred to a separatory funnel and the side product of benzyl alcohol is removed by extraction with ethyl acetate or diethyl ether. After evaporation of the water layer under vacuum (bath a 40° C.) the remaining material is dissolved in 300 mL dichloromethane, insoluble material is then removed by filtration, and the filtrate is evaporated under vacuum (bath at 35° C.). The product is recrystallized from IPA-diethyl ether, and after drying in open air compound C is isolated as off-white crystals. Yield is 32 g (82%).

Example 3

Compound D, by Acid Hydrolysis and Rearrangement:

Example 3 proceeds according to Example 1 with the following exceptions. 5 g of compound C from step 1 is dissolved in 150 mL of concentrated HCl and this solution is stirred at room temperature for 12-24 hours. When by analysis the reaction is complete, the mixture is evaporated to dryness under vacuum (less than 1 torr) at a bath temperature of less than 30° C. The side product of benzyl chloride is distilled off with water, or can be extracted by suitable solvent, for example by dichloromethane. Yield is 95%.

The product after evaporation is worked up promptly in the following step for Compound E according to Example 1. Approximately 1.3 g of solid crystalline L-ergothioneine was obtained. Analysis by HPLC showed approximately 85% pure product. Optical rotation was approximately 80-90°, and the color was light brown. From mother liquors, an additional 0.3 g was obtained, for a total 1.6 g of L-ergothioneine. After recrystallization from water-ethanol 1.3 g (51%) of white crystalline Ergothioneine (E) was obtained; specific optical rotation +126° (c=1, 1N HCl), and confirmed by HPLC-Mass Spectrum and NMR analysis.

Example 4

Compound D, by Acid Hydrolysis and Rearrangement:

Example 4 proceeds according to Example 1 with the following exceptions. 50 g of compound C from step 1 is dissolved in 150 mL of dichloromethane. 500 ml of concentrated HCl is added, and this solution is stirred at room temperature for 12-24 hours. When by analysis the reaction is complete, the mixture is poured into a separatory funnel, the layers separated, and the aqueous phase extracted once more with 100 ml of dichloromethane. After separation of layers, the product (compound D) in aqueous acid is used as is in the final step.

To 100 ml of solution of compound D, 300 ml of distilled water is added followed by 4 g of NH4CNS dissolved in 10 ml of distilled water. The resulting solution is heated for 6 hours at 85-90 C, cooled to room temperature and then worked up as in example 1. Approximately 2.4 g of crude Ergothioneine (E) was obtained.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A method of producing a compound of Formula 4:

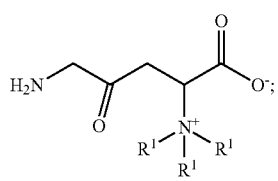

4 comprising
treating a compound of Formula 3 with hydrogen gas, formic acid, or ammonium formate in the presence of a catalyst; or with acid, to form the compound of Formula 4:

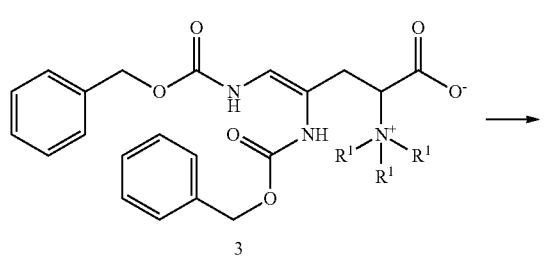

3

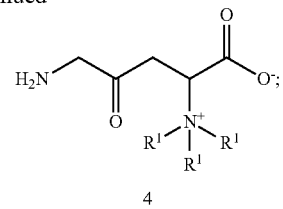

4 wherein each $R^1$ is $(C_{1-4})$alkyl.

2. The method of claim 1 wherein:
the compound according to Formula 3 is:

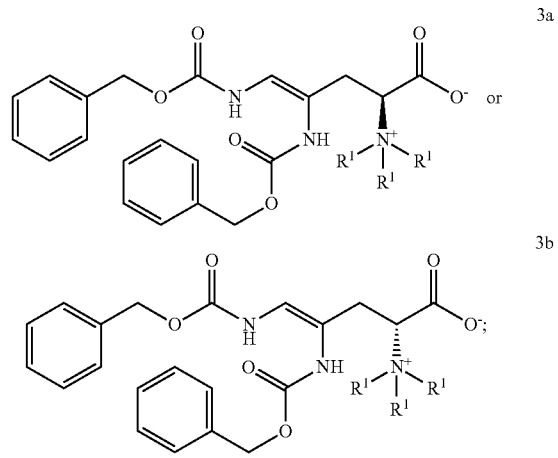

and the compound according to Formula 4 is:

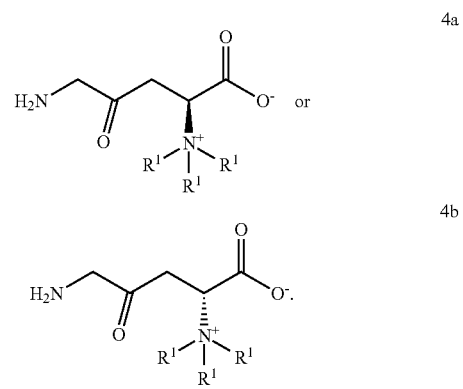

3. The method claim 1 where each $(C_{1-4})$alkyl is unsubstituted.

4. The method claim 1 wherein each $R^1$ is methyl.

5. The method of claim 1 wherein the treatment step is conducted in a solvent selected from the group consisting of water, 1% (w/v) HCl, methanol, ethanol, and 10% to 38% (w/v) HCl in water.

6. The method of claim 1 wherein the catalyst is selected from the group consisting of Pd/C, Pd/C sulfided, Pd/CaSO$_4$, Pd/CaCO$_3$, Pd/CaCO$_3$/Pb and Raney Nickel.

7. The method of claim 1 wherein the treatment step is conducted with an acid.

8. The method of claim 1 wherein the treatment step is conducted in 1% to 38% (w/v) HCl, at a temperature ranging from about 0° C. to 40° C. and for a time ranging from about 1 to 24 hours.

9. The method of claim 1 wherein the treatment step is conducted at a temperature ranging from about 20° C. to about 30° C.

10. The method of claim 1 wherein the treatment step is conducted for a time ranging from about 1 to about 6 hours.

11. The method of claim 1 wherein the treatment step is conducted with hydrogen gas, formic acid, or ammonium formate.

12. A compound of Formula 3:

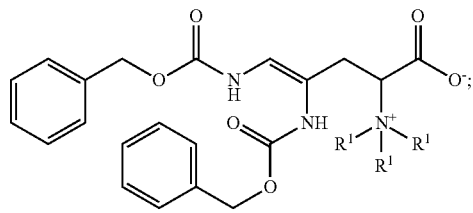

wherein:
    each $R^1$ is $(C_{1-4})$alkyl;
or a salt or tautomer thereof.

13. The compound of claim 12 where the $(C_{1-4})$alkyl are unsubstituted.

14. The compound of claim 12 or 13 having a structure according to Formula 3a or 3b:

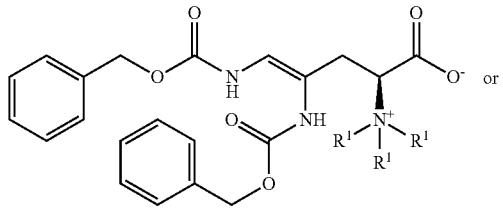

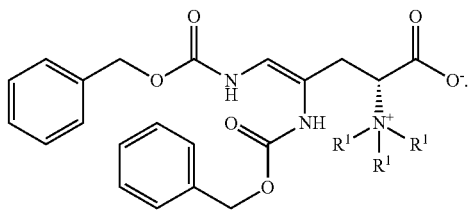

or a salt or tautomer thereof.

15. A compound of Formula 4:

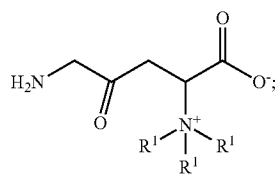

wherein:
    each $R^1$ is $(C_{1-4})$alkyl;
or a salt or tautomer thereof.

16. The compound of claim 15 having a structure according to Formula 4a or 4b:

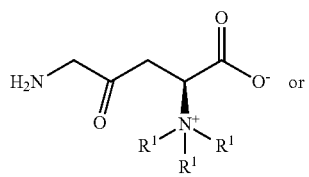

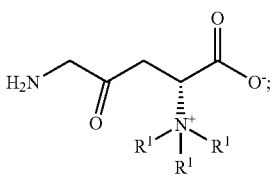

or a salt or tautomer thereof.

* * * * *